United States Patent [19]
Rutkow et al.

[11] Patent Number: 5,356,432
[45] Date of Patent: Oct. 18, 1994

[54] IMPLANTABLE MESH PROSTHESIS AND METHOD FOR REPAIRING MUSCLE OR TISSUE WALL DEFECTS

[75] Inventors: Ira M. Rutkow, Marlboro; Alan W. Robbins, Freehold, both of N.J.

[73] Assignee: C. R. Bard, Inc., Murray Hill, N.J.

[21] Appl. No.: 14,343

[22] Filed: Feb. 5, 1993

[51] Int. Cl.⁵ .................. A61F 2/02; A61F 2/00; A61F 13/00
[52] U.S. Cl. .................. 623/11; 623/1; 606/151; 606/213; 600/37
[58] Field of Search .................. 623/1, 11, 13; 606/1, 606/151, 200, 213, 215; 600/37

[56] References Cited

U.S. PATENT DOCUMENTS

| | | | |
|---|---|---|---|
| 2,836,181 | 5/1958 | Tapp | 623/1 |
| 4,140,126 | 2/1979 | Choudhury | 623/1 |
| 4,452,245 | 6/1984 | Usher | 606/151 |
| 4,710,192 | 12/1987 | Liotta et al. | 623/1 |
| 4,769,038 | 9/1988 | Bendavid et al. | 606/151 |
| 4,781,191 | 11/1988 | Thompson | 606/151 |
| 5,116,357 | 5/1992 | Eberbach . | |
| 5,122,155 | 6/1992 | Eberbach . | |
| 5,141,515 | 8/1992 | Eberbach . | |
| 5,147,374 | 9/1992 | Fernandez | 606/151 |

OTHER PUBLICATIONS

Gilbert, Arthur I., M.D., "Inguinal Hernia Repair: Biomaterials and Sutureless Repair", Perspectives in General Surgery, vol. 2, No. 1, pp. 113-129, 1991.

Primary Examiner—Randall L. Green
Assistant Examiner—Paul Prebilic
Attorney, Agent, or Firm—Wolf, Greenfield & Sacks

[57] ABSTRACT

An implantable prosthesis including a conical mesh plug having a pleated surface which conforms to the contours of the defect being repaired. Mesh filler material positioned in the plug stiffens the implant when it is compressed within the defect.

26 Claims, 2 Drawing Sheets

IMPLANTABLE MESH PROSTHESIS AND METHOD FOR REPAIRING MUSCLE OR TISSUE WALL DEFECTS

FIELD OF INVENTION

The present invention relates to an implantable mesh prosthesis and to a method for repairing muscle or tissue wall defects.

BACKGROUND OF THE INVENTION

Figure 1:
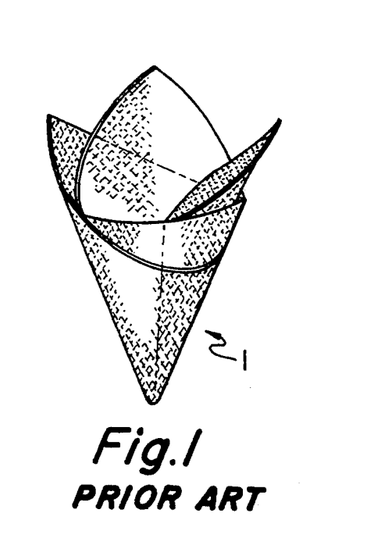
FIG. 1 is an illustration of a prior art conical mesh implant for repairing inguinal hernias.

Various prosthetic mesh materials have been proposed to reinforce the abdominal wall and to close abdominal wall defects. It has been known to fold a sheet of surgical mesh fabric into the multilayer cone configuration 1 illustrated in FIG. 1 and then to insert the mesh plug into a hernia defect to occlude the void. Such a multilayer prosthesis is inherently stiff and may not fully conform to variations in the contour of the defect, leaving gaps between the implant and the abdominal wall that could potentially lead to recurrent herniation. The stiff, multilayered mesh plug also may be susceptible to kinking and buckling during placement.

Other conical mesh plugs have been proposed including a dart which is commercially available from C. R. Bard, Inc., assignee of the present application, under the name "Marlex Mesh Dart". This mesh implant is hot molded into a stiff conical configuration which is non-compressible and which does not conform to irregularities in the muscle or tissue wall defining the defect.

Accordingly, the prior art lacks an implantable mesh plug for filling and repairing muscle and tissue wall ruptures which is adaptable to irregularities in the shape of the defect.

SUMMARY OF THE INVENTION

The present invention is an implantable prosthesis and a method for reinforcing and repairing a weakened muscular wall. The prosthesis is formed of a biologically compatible, flexible and porous surgical mesh fabric suitable for reinforcing tissue and occluding tissue defects. The openings in the mesh prosthesis become completely infiltrated with tissue ingrowth, securing the implant to healthy tissue surrounding the defect. The implantable prosthesis is particularly indicated for the repair of hernias in the abdominal cavity including inguinal (direct and indirect), femoral, incisional and recurrent.

The implantable mesh plug is compressible into a slender shape which fits within a hernia opening, filling all, or at least a significant portion, of the defect. The implant includes a pleated surface which increases the pliability of the implant, allowing the prosthesis to conform to irregularities in the tissue or muscle wall surrounding the opening. A filler body contained within the plug imparts bulk to the device, improving its handling characteristics. The filler also stiffens the implant when it is compressed within the rupture, ensuring a snug fit of the implant against the tissue or wall structure defining the defect. Portions of the filler material are easily removed allowing the surgeon to customize the stiffness of the implant during the operation without damaging the integrity of the prosthesis.

In one embodiment of the invention, the implantable prosthesis includes a conical plug formed of a knitted polypropylene monofilament mesh fabric. Longitudinally running pleats are hot molded into The mesh body which enhances the flexibility of the implant, allowing the implant to closely match the contour of the herniated opening when compressed within the defect.

In another embodiment of the invention, a filler body is positioned in a mesh cone and packs the implant when the plug is compressed by placement in the narrow hernia opening, providing the bulkiness believed to be essential for non-recurrent repair of abdominal wall hernias. The filler body includes a plurality of petals formed from a surgical mesh fabric which extend upwardly from a central base that is seated in the closed end of the cone. The flexible petals curve outwardly and upwardly, pressing against the inner walls of the mesh plug when the implant is positioned within the narrow hernia defect.

It is among the general objects of the invention to provide a prosthesis which is suitable for the repair of abdominal wall hernias.

It is another object of the invention to provide a prosthesis which reduces the incidence of recurrent herniation.

An additional object of the invention is to provide a prosthesis which is suitable for the repair of varying sizes and shapes of hernias.

Other objects and features of the present invention will become apparent from the following detailed description when taken in connection with the accompanying drawings which disclose multiple embodiments of the invention. It is to be understood that the drawings are designed for the purpose of illustration only and are not intended as a definition of the limits of the invention.

DESCRIPTION OF THE DRAWINGS

The foregoing and other objects and advantages of the invention will be appreciated more fully from the following drawings in which.

DESCRIPTION OF THE PREFERRED EMBODIMENTS

Figure 2:
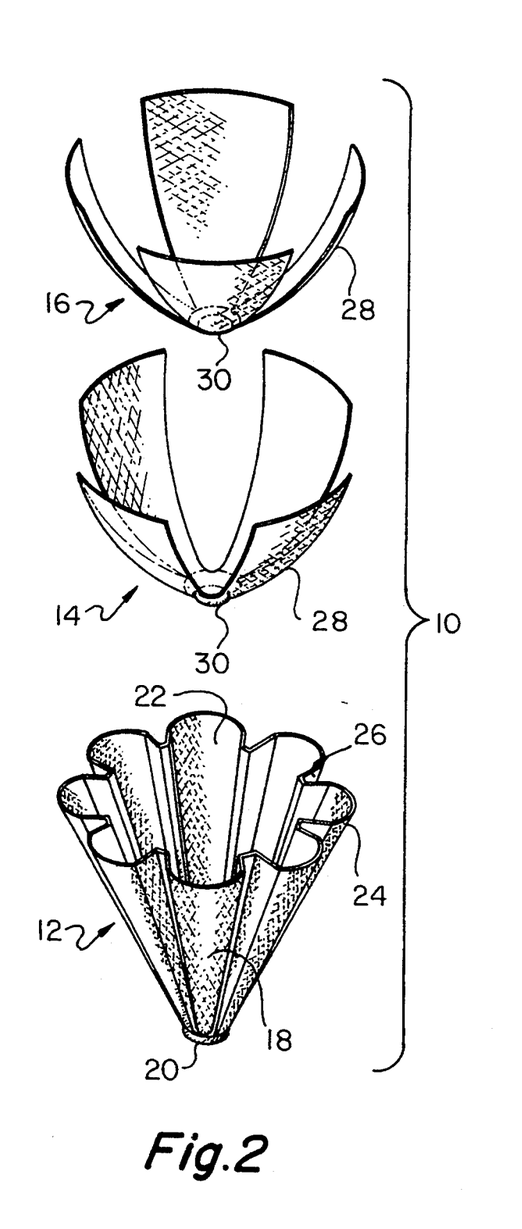
FIG. 2 is an exploded illustration of the implantable mesh prosthesis according to the present invention.
Figure 3:
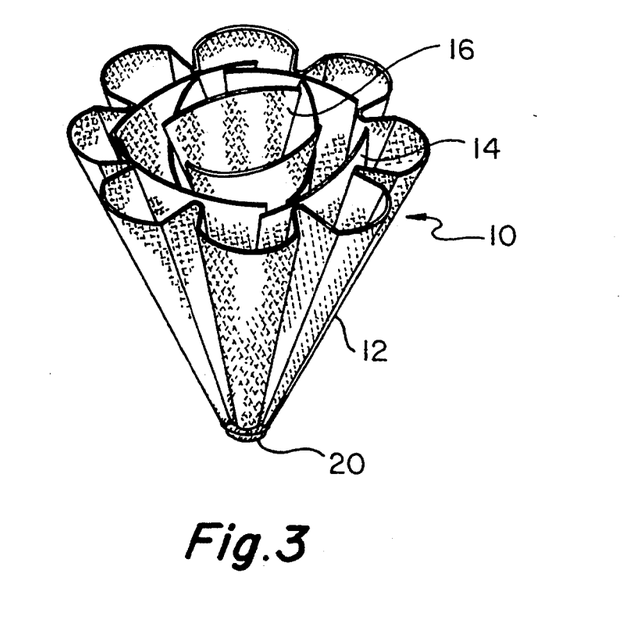
FIG. 3 is an illustration of the implantable mesh prosthesis shown in FIG. 2.

The implantable prosthesis 10 for repairing tissue and muscle wall defects illustrated in FIGS. 2-3 includes a conical plug 12 which is compressible into a slender configuration which approximates the shape of the defect and a pair of inner filler bodies 14 and 16 which impart bulk and stiffen the implant when it is confined within the narrow hernia opening. The surface of the conical plug is pleated 18 which enhances the flexibility and pliability of the implant, allowing the device to conform to irregularities in the shape of the hernia without kinking. The tight and contiguous fit minimizes the formation of gaps between the implant and the surrounding tissue which could potentially lead to recurrent herniation. The conical plug is expected to minimize dissection as compared to classic herniorrhaphy and to permit use of a tension-free repair (e.g., without requiring the approximation of unapposed tissues as in the traditional Cooper ligament technique). Procedures involving the conical mesh plug also are expected to result in reduced patient discomfort, faster recovery, decreased recurrence and a lower incidence of complications.

The plug preferably is formed by hot molding a single circular sheet of surgical mesh fabric into a cone. Other plug configurations, such as a truncated cone or a cylinder, also are contemplated for use in the present invention. The plug has a blunt closed end 20 which minimizes injury to the surgical area when the prosthesis is implanted. The central portion of the plug is hollow and defines a cavity 22 which may be provided with filler material which increases the bulk and stiffness of the plug when compressed within the implant.

Pleats 18 are hot molded into the mesh body and are carried on both the inner and outer surfaces of the prosthesis. The pleats enhance the flexibility and pliability of the plug, allowing the cone to conform to various irregularities in the contour of the defect. The pleats 18 illustrated in FIGS. 2–3 are formed by alternating rounded peaks 24 and pointed valleys 26, similar in appearance to a corrugated surface, which taper inwardly towards the closed end of the plug. Other pleat configurations also may be used so long as the selected pleat allows the plug to closely conform to an irregular defect contour. The pleats preferably are provided about the entire surface of the plug so that any portion of the cone has the ability to conform to a localized irregularity in the tissue or muscle structure defining the defect. Alternatively, the pleats may be provided on only that limited portion of the plug which is likely to encounter the irregular topography or which will require enhanced flexibility.

The conical plug may be provided with one or more mesh filler bodies 14, 16 which stiffen and pack the implant when it is compressed within the defect, compensating for the decrease in rigidity exhibited by the single plug as opposed to the prior art multilayer cones. The inner filler bodies consist of a plurality of mesh petals which extend upwardly from the closed end 20 of the plug into the hollow cavity. The petals 28 may be rounded, as illustrated, or may have an elongated thin configuration similar to a ribbon or strip of mesh. Other configurations of mesh filler also are contemplated.

In one embodiment, the mesh filler bodies 14, 16 are formed from circular sheets of surgical mesh fabric which have been die cut to provide a central base 30 and a plurality of laterally spaced petals 28 as illustrated in FIG. 2. The petals 28 may be pinched together to form a thin insert, facilitating placement in the plug. The components may be joined together by suturing the superposed bases to the rounded tip of the plug. Other means of attachment may be utilized, for example by bonding or stapling the mesh pieces together. In this arrangement, the flexible petals preferably spread outwardly against the inner surface of the conical plug, packing and stiffening the implant when it is compressed.

The first and second filler bodies 14, 16 are offset, preferably by 45° as shown in FIG. 2, ensuring that the filler petals 28 provide relatively uniform packing along the inner surface of the conical plug. Using the internal filler bodies to impart rigidity to the implant, rather than stiffening the conical plug itself, reduces the likelihood that the prosthesis will kink or buckle when fitted in an irregular opening. Providing filler in the center of the implant also eliminates regions of dead or open space which may weaken the prosthetic repair. Although two inner filler bodies are illustrated, additional filler bodies may be provided for applications requiring increased stiffness and bulkiness of the implant. In those situations where only limited packing is required, one filler body may suffice.

The conical plug 12 and inner filler bodies 14, 16 are formed of a tissue infiltratable fabric which allows sufficient tissue ingrowth to secure the prosthesis to healthy tissue surrounding the defect site. The fabric preferably is a knitted polypropylene monofilament mesh fabric such as Marlex ® mesh available from C. R. Bard, Inc. When implanted, the polypropylene mesh stimulates an inflammatory reaction which promotes rapid tissue ingrowth into and around the mesh structure. Alternatively, other surgical materials which are suitable for tissue reinforcement and defect closure may be utilized including Prolene ®, Dacron ®, Teflon ® and Merselene ®. It also is contemplated that the mesh fabric may be formed from multifilament yarns and that woven, molded and other recognized methods of forming prosthetic mesh materials would be suitable. Other tissue wall reinforcement materials also may be used as would be apparent to those of skill in the art.

In a representative procedure, the conical plug is formed by hot molding a circular sheet of Marlex ® knitted polypropylene monofilament mesh fabric into a cone configuration. The cone is then placed in a fixture having fins which project into the mesh fabric forming rounded pleats. The implant is baked and then allowed to cool resulting in a hot molded plug with the desired pleated surface. The inner filler bodies are formed by die cutting two circular sheets of Marlex ® into a cloverleaf arrangement with a central base and four spaced, laterally extending petals. The sheets are superposed offset 45° and then inserted into the cone so that the base seats against the closed end of the plug and the petals curve outwardly and upwardly in the direction of the open end of the plug. The plug may be subject to a final heat treatment to set the cone and filler bodies in the desired configuration. The resulting implant includes a hot molded conical plug with a pleated surface which conforms to the varying contour of a defect and a pair of filler bodies which stiffen the prosthesis when it is compressed in the narrow defect.

Figure 4:
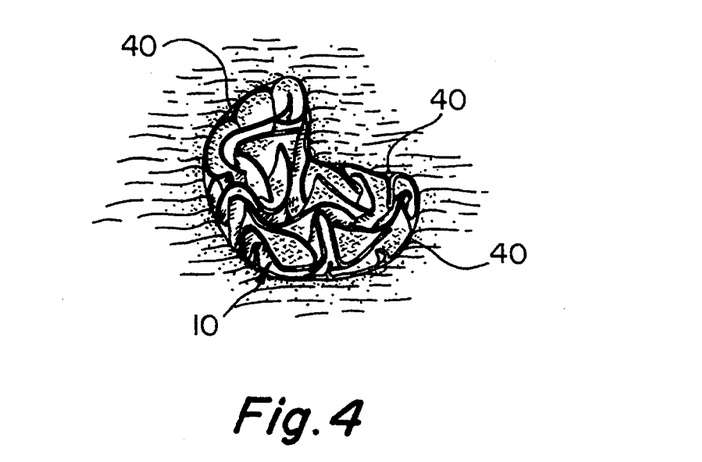
FIG. 4 is an illustration of the implantable prosthesis according to the present invention positioned within an irregular shaped hernia defect and closely conforming to the contours of the rupture.

The close fit of the implantable prosthesis 10 in an irregular opening 40 is illustrated in FIG. 4. The pleated conical plug is extremely pliable, allowing localized portions of the implant to adapt to the irregular contour 40 of the defect. The surface of the implanted conical plug is substantially flush with the tissue surrounding the defect, providing a contiguous and tight fit which is believed to improve the likelihood of a permanent, non-recurrent repair.

In a representative inguinal repair, the hernia region is reached by an anterior surgical approach. For indirect hernias, the lipoma of the cord and the sac are dissected free. The implant, preferably formed of a knitted polypropylene monofilament fabric, is inserted through the internal ring, blunt end first, and positioned just beneath the crura. For direct hernias, the defect is circumscribed at its base and the contents fully reduced. The conical mesh plug is then inserted through the opening until the base lies flush with or slightly beyond the margin of the defect. The compressed implant conforms to the defect shape, providing a snug fit of the plug within the abdominal wall defect.

The stiffness of the compressed plug may be adjusted by snipping off individual leaves of the inner filler body if the surgeon determines that the implant otherwise will become too tightly packed. Depending upon the type of hernia being repaired and the practice of the surgeon, the conical plug and, or alternatively, individual leaves of the filler body, may be sutured to surrounding tissue. Each of the petals may be sutured or otherwise joined to neighboring tissue after implantation without drawing the entire filler body towards the suture site, reducing the likelihood of overpacking a portion of the plug which potentially could lead to recurrent herniation. A separate flat mesh overlay may be placed over the base of the conical implant to reinforce the internal ring and the inguinal canal. The overlay is shaped to match the configuration of the inguinal canal. A slit is spreadable to allow positioning of the spermatic cord in the centered hole. The slit section is then sutured together, preferably using a nonabsorbable monofilament thread, providing a prosthetic reinforcement of the inguinal canal and the internal ring. Within a short period of time, fibroblastic proliferation and collagen formation will penetrate the mesh, securely anchoring the implant in place.

In a representative embodiment, the implantable prosthesis includes a conical plug formed from Marlex ® knitted monofilament polypropylene mesh fabric having a height of 1.0 inch and a base diameter of 1.0 inch. Pleats having a depth of 0.40 inches and a width of 0.068 inches are provided along the surface of the plug. The filler bodies are formed from 1.8 inch diameter pieces of Marlex ® mesh which have been die cut to provide the desired petal arrangement.

The present invention therefore provides a prosthetic implant, amongst which are certain of the following advantages. The mesh plug is compressible into varying sizes and shapes, allowing a single standardized plug, or at most a nominal range of sizes, to satisfactorily repair most commonly encountered hernias. The pleated surface is extremely pliable so that the plug conforms to localized variations in the tissue or muscle wall defining the defect. The stiffness and bulkiness believed to be important for a secure repair is provided by the inner filler bodies without detracting from the flexibility of the single layer plug.

The composite of the present invention is particularly indicated for repair of abdominal wall defects such as inguinal (direct and indirect), femoral, incisional and recurrent hernias. It also is contemplated that the implantable prosthesis would have applications in laparoscopic procedures.

It should be understood that the foregoing description of the invention is intended merely to be illustrative thereof and that other equivalents, embodiments and modifications of the invention may be apparent to those skilled in the art.

We claim:

1. An implantable prosthesis for repairing a tissue or muscle wall defect, comprising:
a flexible plug, formed of a surgical mesh fabric having openings therein for tissue ingrowth, and constructed and arranged to securely fit within and occlude the tissue or muscle wall defect wherein at least a portion of said flexible plug includes a pleated surface which allows radial into the defect without kinking or buckling so that said plug conforms to irregularities in the tissue or muscle wall defining the defect, said flexible plug being compressible radially upon insertion into the defect from a first configuration which is larger than the defect to a second configuration which closely approximates the shape of the defect.

2. The implantable prosthesis recited in claim 1 wherein said flexible plug includes a conical plug.

3. The implantable prosthesis recited in claim 1 wherein said entire plug is pleated.

4. The implantable prosthesis recited in claim 1 wherein said plug includes a closed rounded end, an open end and a cavity extending therebetween, and further includes a plurality of filler material positioned within said cavity and which stiffens said implantable prosthesis when said plug is compressed into said second configuration.

5. An implantable prosthesis for repairing a tissue or muscle wall defect, comprising:
a flexible plug, formed of a surgical mesh fabric having openings therein for tissue ingrowth, constructed and arranged to securely fit within and occlude the tissue or muscle wall defect, said plug being compressible radially upon insertion into the defect form a first configuration which is larger than the defect to a second configuration which closely approximates the shape of the defect, said plug having an open end and a cavity extending therefrom, wherein at least a portion of said flexible plug includes a pleated surface which is conformable to irregularities in the tissue or muscle wall defining the defect; and
a separate filler body, formed of an implantable material, which is positioned within said cavity and is movable relative to said plug, said separate filler body stiffening said implantable prosthesis when said plug is compressed into said second configuration.

6. The implantable prosthesis recited in claim 5 wherein said filler body is formed of a surgical mesh fabric having opening therein for tissue ingrowth.

7. The implantable prosthesis recited in claim 6 wherein said filler body includes a plurality of mesh petals.

8. The implantable prosthesis recited in claim 7 wherein said plurality of mesh petals spread outwardly towards said plug when said plug is in said first configuration.

9. The implantable prosthesis recited in claim 7 wherein said plurality of mesh petals have a common base.

10. The implantable prosthesis recited in claim 7 wherein said plurality of mesh petals lean against said plug when said plug is in said first configuration.

11. The implantable prosthesis recited in claim 5 wherein said filler body includes a plurality of upstanding mesh strips.

12. The implantable prosthesis recited in claim 11 wherein said flexible plug includes a closed end and said plurality of upstanding mesh strips are attached to said closed end and extend therefrom into said cavity and towards said open end.

13. An implantable prosthesis for repairing a tissue or muscle wall defect, comprising:
a flexible plug, formed of a surgical mesh fabric having openings therein for tissue ingrowth, which tapers outwardly from a closed end to a larger end and having a cavity which is defined therebetween, wherein at least a portion of said tapered plug includes a pleated surface which allows radial compression of said pleated portion of said plug upon insertion into the defect without kinking or buckling so that said plug conforms to irregularities in the tissue or muscle wall defining the defect, said flexible plug being compressible radially upon insertion into the defect from a first configuration which is larger than the defect to a second configuration which approximates the shape of the defect so that said plug securely fits therein and occludes the defect;

a first filler body formed of surgical mesh fabric having openings therein for tissue ingrowth, including a common base and a plurality of petals extending upwardly from said base and being spaced laterally thereabout, said base being supported by said plug so that said plurality of petals project into said cavity, whereby said plurality of petals stiffen said implantable prosthesis when said plug is compressed into said second configuration upon insertion into the defect.

14. The implantable prosthesis recited in claim 13 wherein said petals curve outwardly from said base.

15. The implantable prosthesis recited in claim 13 wherein said common base is attached to said closed end of said plug.

16. The implantable prosthesis recited in claim 13 further comprising a second filler body formed of surgical mesh fabric having openings therein for tissue ingrowth and having a plurality of laterally spaced petals that extend upwardly from a common base, said second filler body being positioned within said first filler body and being offset relative thereto, whereby said first and second filler bodies combine to stiffen said implantable prosthesis when said plug is radially compressed into said second configuration upon insertion into the defect.

17. The implantable prosthesis recited in claim 16 wherein said first and second filler bodies are offset by approximately forty-five degrees relative to one another.

18. An implantable prosthesis for repairing a tissue or muscle wall defect, comprising:

a conical plug, formed of a surgical mesh fabric having openings therein for tissue ingrowth, including an atraumatically configured end, a larger open end and a cavity extending therebetween, said conical plug constructed and arranged to securely fit within and occlude the tissue or muscle wall defect wherein at least a portion of said conical plug includes a pleated surface which allows radial compression of said pleated portion upon insertion of said plug into the defect without kinking or buckling so that said plug conforms to irregularities in the tissue or muscle wall defining the defect, said conical plug being radially compressible upon insertion into the defect from a first configuration which is larger than the defect into a second configuration which approximates the shape of the defect;

a plurality of petals, formed of a surgical mesh fabric having openings therein for tissue ingrowth, being positioned in said cavity and extending upwardly from said atraumatically configured end of said plug and being moveable relative to said plug, whereby said plurality of mesh petals stiffen said implantable prosthesis when said plug is compressed into said second configuration upon insertion into the defect.

19. An implantable prosthesis for repairing a tissue or muscle wall defect, comprising:

a hollow plug, formed of a surgical mesh fabric having openings therein for tissue ingrowth, constructed and arranged to securely fit within and occlude the tissue or muscle wall defect and which is radially compressible upon insertion into the defect from a first configuration which is larger than the defect into a second configuration which approximates the shape of the defect, wherein the surface of said hollow plug further includes means for conforming to irregularities in the tissue or muscle wall defining the defect.

20. An implantable prosthesis for repairing a tissue or muscle wall defect, comprising:

a hollow plug, formed of a surgical mesh fabric having openings therein for tissue ingrowth, constructed and arranged to securely fit within and occlude the tissue or muscle wall defect and which is radially compressible upon insertion into the defect from a first configuration which is larger than the defect into a second configuration which approximates the shape of the defect, the surface of said of hollow plug being conformable to irregularities in the tissue or muscle wall defining the defect.

21. A method of repairing a tissue or muscle wall defect, comprising:

providing an implantable prosthesis including a plug formed of a surgical mesh fabric which is compressible from a first configuration which is larger than the defect into a second configuration which approximates the shape of the defect so that the plug securely fits therein and occludes the defect, the plug including an inner filler body formed of spaced petals of a surgical mesh fabric which stiffen the implantable prosthesis when the plug is compressed into the second configuration;

placing the plug in the defect so that the plug compresses into the second configuration; and detaching one or more petals from the inner filler body to vary the stiffness of the implantable prosthesis.

22. An implantable prosthesis for repairing a tissue or muscle wall defect, comprising:

a hollow conical plug formed of a surgical mesh fabric having openings therein for tissue ingrowth, constructed and arranged to securely fit within and occlude the tissue or muscle walk defect, at least a portion of said hollow conical plug including a plurality of longitudinal pleats which allow radial compression of said pleated portion upon insertion of said plug into the defect so that said pleated portion conforms to irregularities in the contour of the defect, said hollow conical plug being radially compressible from a first configuration which is larger than the defect into a second configuration which closely approximates the shape of the defect.

23. The implantable prosthesis recited in claim 22 wherein said longitudinal pleats have a corrugated configuration.

24. The implantable prosthesis recited in claim 23 wherein said corrugated pleats include alternating peaks and valleys and wherein said peaks are larger than said valleys.

25. The implantable prosthesis recited in claim 22 wherein said hollow plug includes an atraumatically configured end and an opposite end wherein said longitudinal pleats taper inwardly from said opposite end towards said atraumatically configured end.

26. An implantable prosthesis for repairing a tissue or muscle wall defect, comprising:

a single layer conical plug, formed from a surgical mesh fabric having openings therein for tissue ingrowth, including a closed end, a larger open end and a cavity extending therebetween and having a plurality of longitudinal pleats extending between said closed end and said larger open end which allows radial compression of said single layer conical plug upon insertion of said prosthesis into the defect so that said single layer conical plug conforms to irregularities in the contour of the defect without kinking or buckling, said single layer conical plug being radially compressible from a first configuration which is larger than the defect into a second configuration which closely approximates the shape of the defect.

* * * * *

UNITED STATES PATENT AND TRADEMARK OFFICE
CERTIFICATE OF CORRECTION

PATENT NO. : 5,356,432
DATED : October 18, 1994
INVENTOR(S) : Rutkow et al.

It is certified that error appears in the above-indentified patent and that said Letters Patent is hereby corrected as shown below:

Col. 5, Line 63, (claim 1, line 8) after "radial", insert --compression of said pleated portion upon insertion of said plug --.

Col. 6, Line 21, (claim 5, line 8) replace "form" with --from --.

Col. 8, Line 47, (claim 22, line 6) replace "walk" with --wall --.

Signed and Sealed this

Fifth Day of August, 1997

Attest:

BRUCE LEHMAN

Attesting Officer

Commissioner of Patents and Trademarks

/ # REEXAMINATION CERTIFICATE (3125th)
United States Patent [19]
Rutkow et al.

[11] B1 5,356,432
[45] Certificate Issued Feb. 4, 1997

[54] IMPLANTABLE MESH PROSTHESIS AND METHOD FOR REPAIRING MUSCLE OR TISSUE WALL DEFECTS

[75] Inventors: Ira M. Rutkow, Marlboro; Alan W. Robbins, Freehold, both of N.J.

[73] Assignee: C. R. Bard, Inc., Murray Hill, N.J.

Reexamination Request:
No. 90/003,812, May 1, 1995

Reexamination Certificate for:
Patent No.: 5,356,432
Issued: Oct. 18, 1994
Appl. No.: 14,343
Filed: Feb. 5, 1993

[51] Int. Cl.$^6$ .............. A61F 2/02; A61F 2/00; A61F 13/00
[52] U.S. Cl. .............. 623/11; 623/1; 606/151; 606/213; 600/37

[56] References Cited

U.S. PATENT DOCUMENTS

| | | | |
|---|---|---|---|
| 2,836,181 | 5/1958 | Tapp | 623/1 |
| 4,140,126 | 2/1979 | Choudhury | 606/194 |
| 4,452,245 | 6/1984 | Usher | 606/151 |
| 4,710,192 | 12/1987 | Liotta et al. | 623/1 |
| 4,769,038 | 9/1988 | Bendavid et al. | 623/13 |
| 4,781,191 | 11/1988 | Thompson | 606/151 |
| 5,116,357 | 5/1992 | Eberbach | 606/213 |
| 5,122,155 | 6/1992 | Eberbach | 606/213 |
| 5,141,515 | 8/1992 | Eberbach | 606/151 |
| 5,147,374 | 9/1992 | Fernandez | 606/151 |

OTHER PUBLICATIONS

American Heritage Dictionary, Second College Edition, (1982), p. 667.
Gilbert, "Inguinal Hernia Repair: Biomaterials and Sutureless Repair", Perspectives In General Surgery, vol. 2, No. 1, (1991) pp. 113–129.
Rutkow et al, "'Tension Free' Inguinal Herniorrhaphy: The 'Mesh Plug' Technique", The Hernia Center Freehold, NJ, pp. 1–23 and a single page with a photograph, (incomplete copy).
Trabucco, "Routine Sutureless Mesh In Primary Inguinal Hernioplasty", pp. 1–6 and 5 pages with 10 figures on them.
Trabucco, "A New Preperitoneal Plug Technique For Recurrent Groin Hernioplasty", pp. 1–7 and 4 pages with 7 figures on them.
Ira M. Rutkow, MD, MPH, DrPH, and Alan W. Robbins, MD, "Tension–Free" Inguinal Herniorrhapy: A preliminary report on the mesh plug technique, Jul. 1993, pp. 3–8, Surgery, vol. 114, No. 1.

*Primary Examiner*—Paul Prebilic

[57] ABSTRACT

An implantable prosthesis including a conical mesh plug having a pleated surface which conforms to the contours of the defect being repaired. Mesh filler material positioned in the plug stiffens the implant when it is compressed within the defect.

B1 5,356,432

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-18 and 21-26 is confirmed.

Claims 19 and 20 are determined to be patentable as amended.

19. An implantable prosthesis for repairing a tissue or muscle wall defect, comprising:

a hollow plug, formed of a surgical mesh fabric having openings therein for tissue ingrowth, constructed and arranged to securely fit within and occlude the tissue or muscle wall defect and which is radially compressible upon insertion into the defect from a first configuration which is larger than the defect into a second configuration which approximates the shape of the defect, wherein the surface of said hollow plug [further] includes means for conforming to irregularities in the tissue or muscle wall defining the defect *upon insertion of said plug into the defect, said means for conforming making the hollow plug extremely pliable and allowing localized portions of the hollow plug to adapt to irregularities in the tissue or muscle wall defect.*

20. An implantable prosthesis for repairing a tissue or muscle wall defect, comprising:

a hollow plug, formed of a surgical mesh fabric having openings therein for tissue ingrowth, constructed and arranged to securely fit within and occlude the tissue or muscle wall defect and which is radially compressible upon insertion into the defect from a first configuration which is larger than the defect into a second configuration which approximates the shape of the defect, the surface of said [of] hollow plug being conformable to irregularities in the tissue or muscle wall defining the defect *upon insertion of said hollow plug into the defect, said hollow plug being extremely pliable, allowing localized portions of the hollow plug to adapt to irregularities in the tissue or muscle wall defect.*

* * * * *